United States Patent [19]

Axen

[11] 4,191,824

[45] Mar. 4, 1980

[54] 5-HALO PGI COMPOUNDS

[75] Inventor: Udo F. Axen, Plainwell, Mich.

[73] Assignee: The Upjohn Company, Kalamazoo, Mich.

[21] Appl. No.: 959,399

[22] Filed: Nov. 9, 1978

Related U.S. Application Data

[60] Division of Ser. No. 819,857, Jul. 28, 1977, Pat. No. 4,158,667, which is a continuation-in-part of Ser. No. 725,548, Sep. 22, 1976, abandoned, which is a continuation-in-part of Ser. No. 716,972, Aug. 23, 1976, abandoned, which is a continuation-in-part of Ser. No. 655,110, Feb. 4, 1976, abandoned.

[51] Int. Cl.² .......................................... C07D 307/93
[52] U.S. Cl. ................................... 542/429; 542/420; 542/421; 542/422; 542/426; 542/430; 542/431; 260/345.7 P; 260/345.8 P; 260/345.9 P; 260/346.22; 260/346.73
[58] Field of Search ....................... 260/346.22, 346.73, 260/308 D, 345.7 P, 345.8 P, 345.9 P; 542/426, 429

[56] References Cited

PUBLICATIONS

Johnsen, J.A.C.S. 99:12, Jun. 8, 1977, pp. 4102–4104.

*Primary Examiner*—Alan L. Rotman
*Assistant Examiner*—Bernard Dentz
*Attorney, Agent, or Firm*—Morris L. Nielsen

[57] ABSTRACT

Prostaglandin ($PG_1$) derivatives having (1) a 6-keto feature, for example

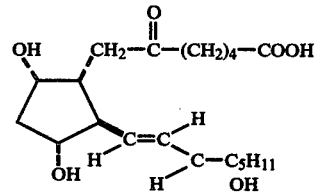

or (2) a 9-deoxy-6,9-epoxy feature together with a 5-halo or 6-hydroxy feature, for example

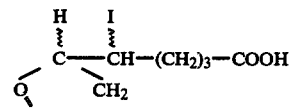

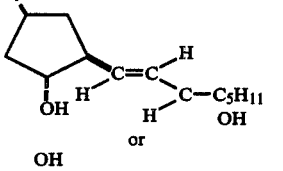

or

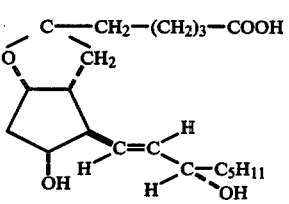

said derivatives having pharmacological activity. Processes for preparing them and the appropriate intermediates are disclosed.

35 Claims, No Drawings

5-HALO PGI COMPOUNDS

CROSS REFERENCE TO RELATED APPLICATIONS

The present application is a divisional application of Ser. No. 819,857, filed July 28, 1977, now U.S. Pat. No. 4,158,667 issued June 19, 1979; which is a continuation-in-part application of Ser. No. 725,548, filed Sept. 22, 1976, now abandoned; which is a continuation-in-part of Ser. No. 716,972, filed Aug. 23, 1976, now abandoned, which was a continuation-in-part of Ser. No. 655,110, filed Feb. 4, 1976, now abandoned.

The present invention relates to prostaglandin analogs, for which the essential material constituting disclosure therefor is incorporated by reference here from U.S. Pat. No. 4,158,667.

I claim:

1. A compound of the formula

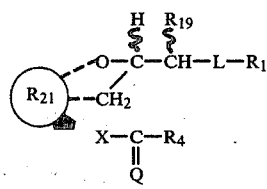

or a mixture comprising that compound and the enantiomer thereof wherein 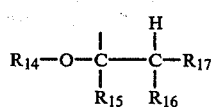 is

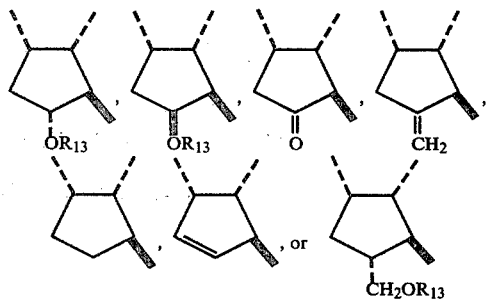

wherein $R_{13}$ is (a) hydrogen, (b) tetrahydropyranyl, (c) tetrahydrofuranyl, (d) 1-ethoxyethyl, (e) a group of the formula $$R_{14}-O-\underset{\underset{R_{15}}{|}}{\overset{\overset{H}{|}}{C}}-\underset{\underset{R_{16}}{|}}{C}-R_{17}$$

wherein $R_{14}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{15}$ and $R_{16}$ are the same or different, being hydrogen, alkyl of one to 4 carbon atoms, inclusive, phenyl or phenyl substituted with one, 2, or 3 alkyl of one to 4 carbon atoms, inclusive, or, when $R_{15}$ and $R_{16}$ are taken together, $-(CH_2)a-$ or $-(CH_2)b-O-(CH_2)c-$ wherein a is 3, 4, or 5, b is one, 2, or 3, and c is one, 2, or 3, with the proviso that b plus c is 2, 3, or 4, and wherein $R_{17}$ is hydrogen or phenyl, or (f) carboxyacyl including

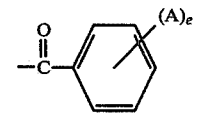

wherein "A" is alkyl of one to 4 carbon atoms, inclusive, bromo, phenylalkyl of 7 to 10 carbon atoms, inclusive, or nitro, and "e" is zero to 5, inclusive, provided that not more than two A's are other then alkyl, and that the total number of carbon atoms in the A's does not exceed 10 carbon atoms,

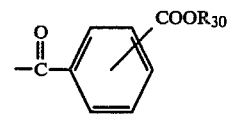

wherein $R_{30}$ is alkyl of one to 4 carbon atoms, inclusive,

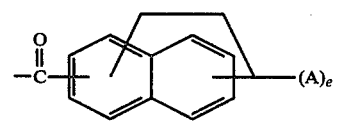

wherein "A" and "e" are as defined above, or

wherein $R_{31}$ is alkyl of one to 7 carbon atoms, inclusive, wherein L is
(1) $-(CH_2)d-C(R_2)_2-$
(2) $-CH_2-O-CH_2-Y-$ or
(3) $-CH_2CH=CH-$ wherein d is zero to 5, $R_2$ is hydrogen, methyl, or fluoro, being the same or different with the proviso that one $R_2$ is not methyl when the other is fluoro, and Y is a valence bond, $-CH_2-$, or $-(CH_2)_2-$, wherein Q is

wherein $R_8$ is hydrogen or alkyl of one to 4 carbon atoms, inclusive, and $R_{13}$ is as defined above, wherein $R_1$ is
(1) $-COOR_3$
(2) $-CH_2OH$
(3) $-CH_2N(R_{19})(R_{18})$

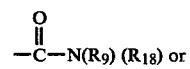

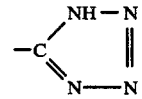

wherein $R_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive, (g) [structure: phenyl-NH-C(=O)-phenyl-NH-C(=O)-CH₃]

(h) [structure: phenyl-NH-C(=O)-phenyl]

(i) [structure: phenyl-NH-C(=O)-CH₃]

(j) [structure: phenyl-NH-C(=O)-NH₂]

(k) [structure: phenyl-CH=N-NH-C(=O)-NH₂]

(l) [structure: 2-naphthyl]

(m) [structure: -CH(R₁₁)-C(=O)-R₁₀]

wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl, or (n) a pharmacologically acceptable cation, wherein $R_8$ is hydrogen, methyl, or ethyl, and wherein $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive; wherein $R_4$ is (1) [structure: -C(R₅)(R₆)-CgH₂g-CH₃]

(2) [structure: -C(R₅)(R₆)-Z-phenyl(T)s] or (3) [structure: -CH₂-CH=CH-CH₂CH₃ (cis)]

wherein $C_gH_{2g}$ is alkylene of one to 9 carbon atoms, inclusive, with one to 5 carbon atoms, inclusive, in the chain between $-CR_5R_6-$ and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jH_2$ is a valence bond or alkylene of one to 9 carbon atoms, inclusive, with one to 6 carbon atoms, inclusive between $CR_5R_6-$ and the phenyl ring; wherein T is alkyl of one to 4 carbon atoms, inclusive, fluoro, chloro, trifluoromethyl, or $-OR_7-$ wherein $R_7$ is alkyl of one to 4 carbon atoms, inclusive, and s is zero, one, 2, or 3, with the proviso that not more than two T's are other than alkyl and when s is 2 or 3 the T's are either the same or different;

wherein $R_{19}$ is chloro, bromo, or iodo with the proviso that $R_{19}$ is not bromo when $R_{20}$ is

[cyclopentane structure with OH]

Q is [structure with H, OH]

L is $-(CH_2)_3-$, $R_4$ is n-pentyl, and X is $-C\equiv C-$; and wherein X is
 (1) trans—CH=CH—
 (2) cis—CH=CH—
 (3) —C≡C— or
 (4) —CH₂CH₂—.

2. A compound according to claim 1 wherein $R_{13}$ is hydrogen.

3. A compound according to claim 2 wherein $R_{21}$ is

[cyclopentane structure with OH]

4. 5ξ-Iodo-9-deoxy-6ξ,9α-epoxy-11β-PGF₁, methyl ester, compounds according to claim 3.

5. A compound according to claim 2 wherein $R_{21}$ is

[cyclopentane structure with =O]

6. A compound according to claim 2 wherein $R_{21}$ is

[cyclopentane structure with =CH₂]

7. A compound according to claim 2 wherein $R_{21}$ is

[cyclopentane structure]

8. A compound according to claim 2 wherein 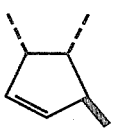 is

9. A compound according to claim 2 wherein 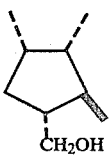 is

10. A compound according to claim 2 wherein 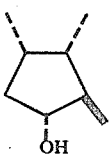 is

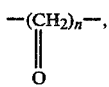

wherein L is

n being 3, 4, or 5, wherein Q is or

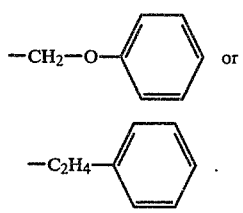

wherein $R_8$ is limited to hydrogen, methyl, or ethyl, and
wherein $R_4$ is n-pentyl, 1,1-dimethylpentyl, 1,1-difluoropentyl,

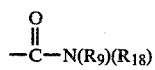

11. A compound according to claim 10 wherein $R_1$ is $$-\overset{O}{\underset{\|}{C}}-N(R_9)(R_{18})$$

wherein $R_{19}$ and $R_{18}$ are as defined in claim 1.

12. 5ξ-Iodo-9-deoxy-6ξ,9α-epoxy-PGF$_1$, amide, compounds according to claim 11.
13. 5ξ-Iodo-9-deoxy-6ξ,9α-epoxy-PGF$_1$, methylamide, compounds according to claim 11.
14. 5ξ-Iodo-9-deoxy-6ξ,9α-epoxy-PGF$_1$, n-butylamide, comcpounds according to claim 11.
15. 5ξ-Iodo-9-deoxy-6ξ,9α-epoxy-PGF$_1$, benzylamide, compounds according to claim 11.
16. 5ξ-Iodo-9-deoxy-6ξ,9α-epoxy-PGF$_1$, anilide, compounds according to claim 11.
17. A compound according to claim 10 wherein $R_1$ is —COOR$_3$ wherein $R_3$ is as defined in claim 1.
18. A compound according to claim 17 wherein X is —C≡C—.
19. 5ξ-Bromo-9-deoxy-6ξ,9α-epoxy-15(R)-13,14-didehydro-PGF$_1$, methyl ester, compounds according to claim 2.
20. A compound according to claim 17 wherein X is trans-CH=CH—.
21. A compound according to claim 20 wherein $R_3$ is

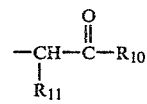

wherein $R_{10}$ and $R_{11}$ are as defined in claim 1.
22. 5ξ-Iodo-9-deoxy-6ξ,9α-epoxy-PGF$_1$, p-phenylphenacyl ester, compounds according to claim 21.
23. A compound according to claim 20 wherein $R_3$ is hydrogen, alkyl of one to 12 carbon atoms, inclusive, or a pharmacologically acceptable cation.
24. A compound according to claim 23 wherein $R_3$ is hydrogen, methyl, or a pharmacologically acceptable cation.
25. 5ξ-Iodo-9-deoxy-6ξ,9α-epoxy-PGF$_1$, compounds according to claim 24.
26. 5ξ-Bromo-9-deoxy-6ξ,9α-epoxy-PGF$_1$, methyl ester, compounds according to claim 24.
27. 5ξ-Iodo-9-deoxy-6ξ,9α-epoxy-PGF$_1$, methyl ester, compounds according to claim 24.
28. 5ξ-Iodo-9-deoxy-6ξ,9α-epoxy-17-phenyl-18,19,20-trinor-PGF$_1$, methyl ester, compounds according to claim 96.
29. A compound according to claim 1 wherein $R_{13}$ is tetrahydropyranyl.
30. A compound according to claim 1 wherein $R_{13}$ is carboxyacyl as defined in claim 1.
31. 5ξ-Iodo-9-deoxy-6ξ,9α-epoxy-PGF$_1$, methyl ester, 11,15-bis(4-bromobenzoate), compounds according to claim 30.
32. A compound according to claim 2 wherein $R_4$ is

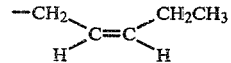

33. 5ξ-Iodo-9-deoxy-6ξ,9α-epoxy-17,18-didehydro-PGF$_1$, methyl ester, compounds according to claim 32.
34. 5ξ-Iodo-9-deoxy-6ξ,9α-epoxy-15-deoxy-PGF$_1$, methyl ester, compounds according to claim 24.
35. 5ξ-Iodo-9-deoxy-6ξ,9α-epoxy-PGF$_1$, p-(p-acetamidobenzamido)-phenyl ester, compounds according to claim 20.

* * * * *

UNITED STATES PATENT OFFICE
CERTIFICATE OF CORRECTION

Patent No. 4,191,824          Dated  4 March 1980

Inventor(s) Udo F. Axen

It is certified that error appears in the above-identified patent and that said Letters Patent are hereby corrected as shown below:

In the abstract, that portion of the first formula reading

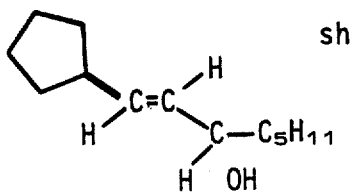     should read     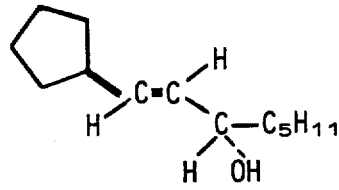     ;

that portion of the second formula reading

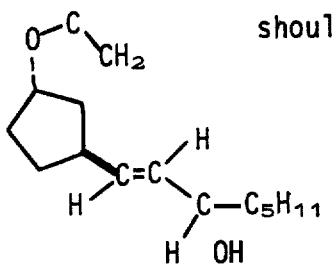     should read     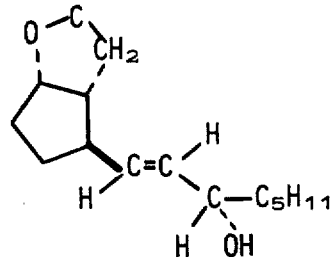     ;

that portion of the third formula reading

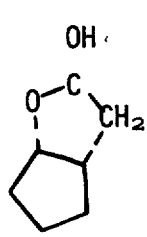     should read     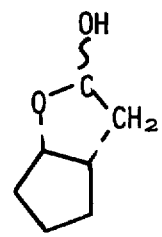     ;

UNITED STATES PATENT OFFICE
CERTIFICATE OF CORRECTION

Patent No. 4,191,824                     Dated 4 March 1980

Inventor(s) Udo F. Axen

It is certified that error appears in the above-identified patent and that said Letters Patent are hereby corrected as shown below:

Column 1, lines 23-28, that portion of the formula reading

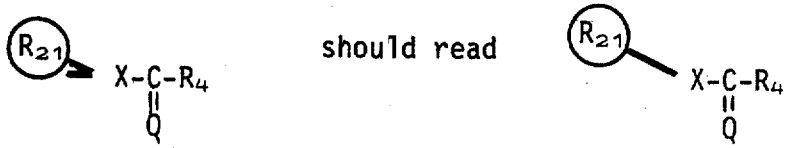

Column 2, line 55, "$-CH_2N(R_{19})(R_{18})$" should read -- $-CH_2N(R_9)(R_{18})$ --;
Column 3, line 36, "wherein $R_8$ is" should read -- wherein $R_9$ is --;
Column 4, line 9, " $R_{20}$ " should read -- $R_{21}$ --;

Column 5, lines 31-39, should read -- wherein L is $-(CH_2)_n-$, n being 3, 4, or 5, wherein Q is $\overset{\|}{O}$ or $R_8\diagup\diagdown OH$ -- instead of as appears in the patent;

line 67, "wherein $R_{19}$ and $R_{18}$" should read -- wherein $R_9$ and $R_{18}$ --.

*Signed and Sealed this*

*Twenty-first* Day of *April 1981*

[SEAL]

*Attest:*

RENE D. TEGTMEYER

*Attesting Officer*     *Acting Commissioner of Patents and Trademarks*